(12) United States Patent
Yamano

(10) Patent No.: US 8,101,580 B2
(45) Date of Patent: Jan. 24, 2012

(54) THERAPEUTIC AGENT FOR IRRITABLE BOWEL SYNDROME

(75) Inventor: Mayumi Yamano, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 933 days.

(21) Appl. No.: 11/911,668

(22) PCT Filed: Apr. 19, 2006

(86) PCT No.: PCT/JP2006/308173
§ 371 (c)(1),
(2), (4) Date: Oct. 16, 2007

(87) PCT Pub. No.: WO2006/115135
PCT Pub. Date: Nov. 2, 2006

(65) Prior Publication Data
US 2009/0093415 A1 Apr. 9, 2009

(30) Foreign Application Priority Data
Apr. 21, 2005 (JP) ................................. 2005-123682

(51) Int. Cl.
*A61K 38/08* (2006.01)
*A61K 35/37* (2006.01)

(52) U.S. Cl. ........................ 514/21.6; 530/328; 424/551

(58) Field of Classification Search ........................ None
See application file for complete search history.

(56) References Cited

U.S. PATENT DOCUMENTS

| | | | |
|---|---|---|---|
| 4,563,475 A * | 1/1986 | Kuhla et al. | .................. 514/427 |
| 2005/0049240 A1 | 3/2005 | Gribenow et al. | |
| 2005/0124614 A1 | 6/2005 | Gangloff et al. | |
| 2009/0163545 A1 | 6/2009 | Goldfarb | |

FOREIGN PATENT DOCUMENTS

| | | |
|---|---|---|
| EP | 1 872 795 | 1/2008 |
| JP | 7-258081 | 10/1995 |
| JP | 2005-510475 | 4/2005 |
| WO | 91/02746 | 3/1991 |
| WO | 92/07830 | 5/1992 |
| WO | 92/09626 | 6/1992 |
| WO | 98/07718 | 2/1998 |
| WO | 00/09115 | 2/2000 |
| WO | 02/40469 | 5/2002 |
| WO | 02/40475 | 5/2002 |
| WO | 02/49644 | 6/2002 |
| WO | 03/029221 | 4/2003 |
| WO | 2004/004727 | 1/2004 |
| WO | 2006/045096 | 4/2006 |
| WO | 2006/097323 | 9/2006 |
| WO | 2006/115135 | 11/2006 |
| WO | 2007/105989 | 9/2007 |
| WO | 2007/133108 | 11/2007 |
| WO | 2008/112715 | 9/2008 |

OTHER PUBLICATIONS

M.R. Martins et al. Peptides (2005) 26(12), pp. 2525-2529.*

Pinski, et al., "High potency of a new bombesin antagonist (RC-3095) in inhibiting serum gastrin levels; comparison of . . . ", Regulatory Peptides, No. 41 (1992) 185-93.

Ishikawa, "A Clinical Study of Regulation of Motility of Digestive Tract by Gastrointestinal Hormones", Jap. J. Med., vol. 14, No. 1 (1975) 21-5.

Dietrich, et al., "Effects of BIM26226, a potent and specific bombesin receptor antagonist, on amylase release and . . . ", Regulatory Peptides, vol. 53 (1994) 165-73.

Talley, "Pharmcologic Therapy for the Irritable Bowel Syndrome", The American Journal of Gastroenterology, vol. 98, No. 4 (2003) 750-58.

Fukudo, et al., "Impact of corticotropin-releasing hormone on gastrointestinal motility and . . . ", Gut, vol. 42 (1998) 845-49.

Merali, et al., "Aversive and Appetitive Events Evoke the Release of Corticotropin-Releasing Hormone and . . . ", The Journal of Neuroscience, vol. 18, No. 12 (1998) 4758-66.

Garrido, et al., "Gastrin-releasing peptide mediated regulation of 5-HT neuronal activity in the . . . ", Life Sciences, vol. 70 (2002) 2953-66.

Yagi, et al., "Perinatal Changes in Bombesin-Stimulated Muscle Contraction in Rabbit Stomach and Colon", Gastroenterology, vol. 100, No. 4 (1991) 980-85.

Vadokas, et al., "Effects of gastrin-releasing peptide (GRP) on the mechanical activity of the human ileocaecal region in vitro", Neurogastroenterol Mot., vol. 9, No. 4 (1997) 265-70.

Suzuki, et al., "Synergistic Interaction Between VIP-Related Peptides and Bombesin on . . . " Annals New York Academy of Sciences, vol. 921, 420-24.

Reile, et al., "Characterization of High-Affinity Receptors for Bombesin/Gastrin Releasing Peptide . . . ", The Prostate, vol. 25 (1994), 29-38.

Koppan, et al., "Bombesin/Gastrin-Releasing Peptide Antagonists RC-3095 and RC-3940-II Inhibit Tumor Growth and . . . ", Cancer, vol. 83, No. 7 (1998) 1335-43.

Chatzistamou, et al., "Inhibition of Growth of OV-1063 human epithelial ovarian cancers and . . . ", British Journal of Cancer, vol. 83, No. 7 (2000) 906-13.

Kahan, et al., "Inhibition Growth of MDA-MB-468 Estrogen-Independent Human Breast Carcinoma by . . . ", Cancer, vol. 88, No. 6 (2000) 1384-92.

Valentine, et al., "CP-70,030 and CP-75,998; The First Non-Peptide Antagonists of Bombesin and . . . ", Bioorganic & Medicinal Chemistry Letters, vol. 2, No. 4 (1992) 333-38.

Ashwood, et al., "PD 176252—The First High Affinity Non-peptide Gastrin-Releasing Peptide (BB2) Receptor Antagonist", Bioorganic & Medicinal Chemistry Letters, vol. 8 (1998) 2589-94.

(Continued)

*Primary Examiner* — Cecilia J Tsang
*Assistant Examiner* — Satyanarayana Gudibande
(74) *Attorney, Agent, or Firm* — Fitzpatrick, Cella, Harper & Scinto

(57) ABSTRACT

It was shown that bombesin 2 (BB2) receptor antagonists typified by RC-3095 are therapeutic agents for irritable bowel syndrome (IBS), and show excellent efficacy in treating both an abdominal symptom and bowel movement disorder. Thus, the present invention provides a therapeutic agent for irritable bowel syndrome (IBS) which comprises, as an active ingredient, a bombesin 2 (BB2) receptor antagonist as well as a method for treating IBS.

5 Claims, 5 Drawing Sheets

OTHER PUBLICATIONS

Shivarama, et al., "Studies on nitrophenylfuran derivatives Part XII. Synthesis, characterization, antibacterial and . . . ", Il Farmaco, vol. 56, No. 10 (2001) 919-27.

Foloppe, et al., "Discovery and functional evaluation of diverse novel human CB1 receptor ligands", Bioorganic & Medicinal Chemistry Letters, vol. 19 (2009) 4183-90.

STN Registry, 931939-66-1 (2007).

STN Registry, 931315-65-0 (2007).

STN Registry, 902607-43-6 (2006).

Office Action for corresponding Japanese application JP2007-514619 (with English translation). 2011.

Sogo Rinsho, vol. 51, Supplementary Issue (2002) 1416-19 (with English abstract).

Extended European Search Report dated Aug. 4, 2011.

Yu, Chinese Medical Journal, vol. 120, No. 23 (2007) 2143-45.

\* cited by examiner

[Fig. 1]
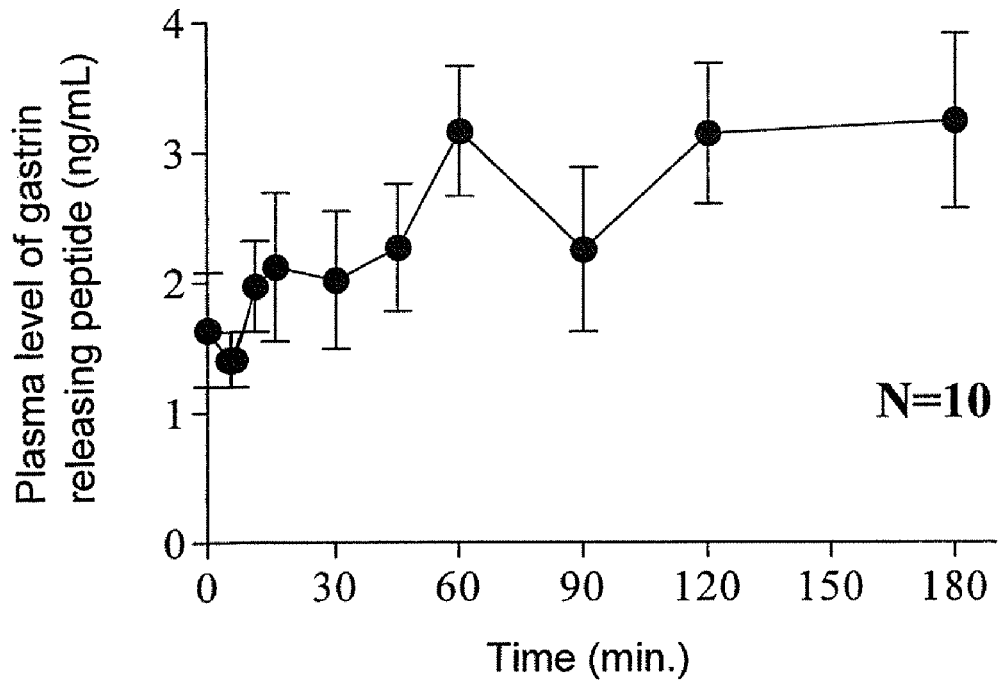
[Fig. 2]
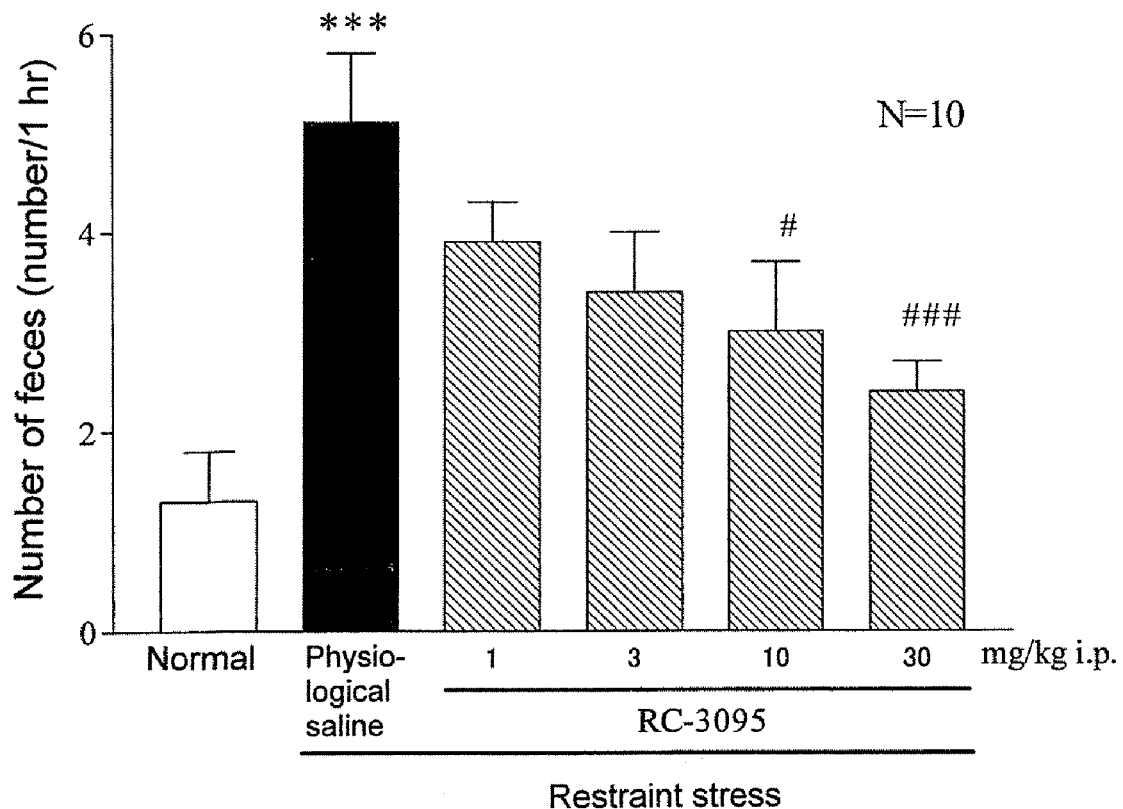

[Fig. 3]
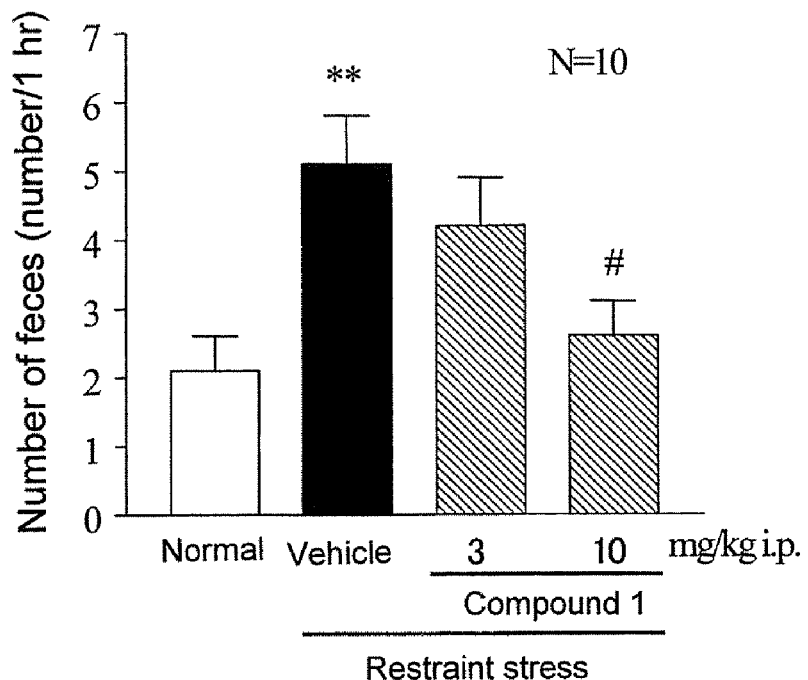
[Fig. 4]
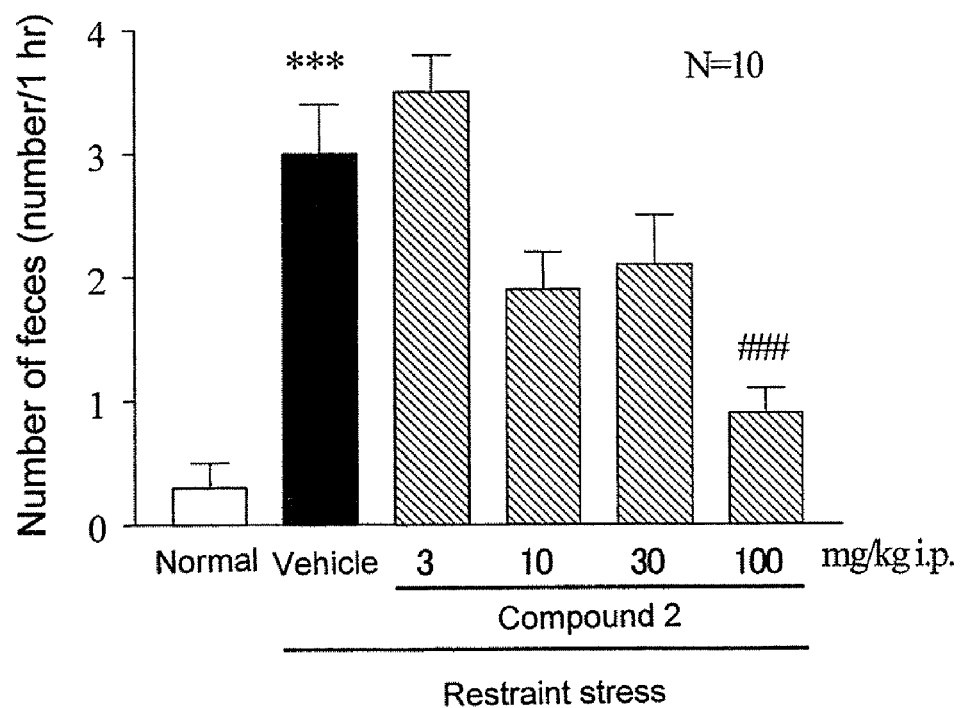

[Fig. 5]
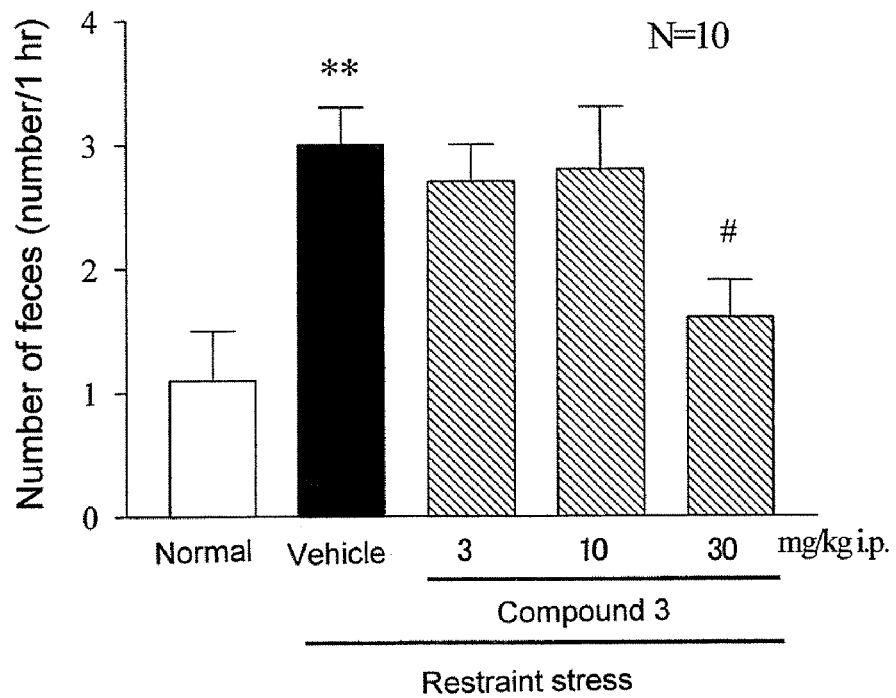
[Fig. 6]
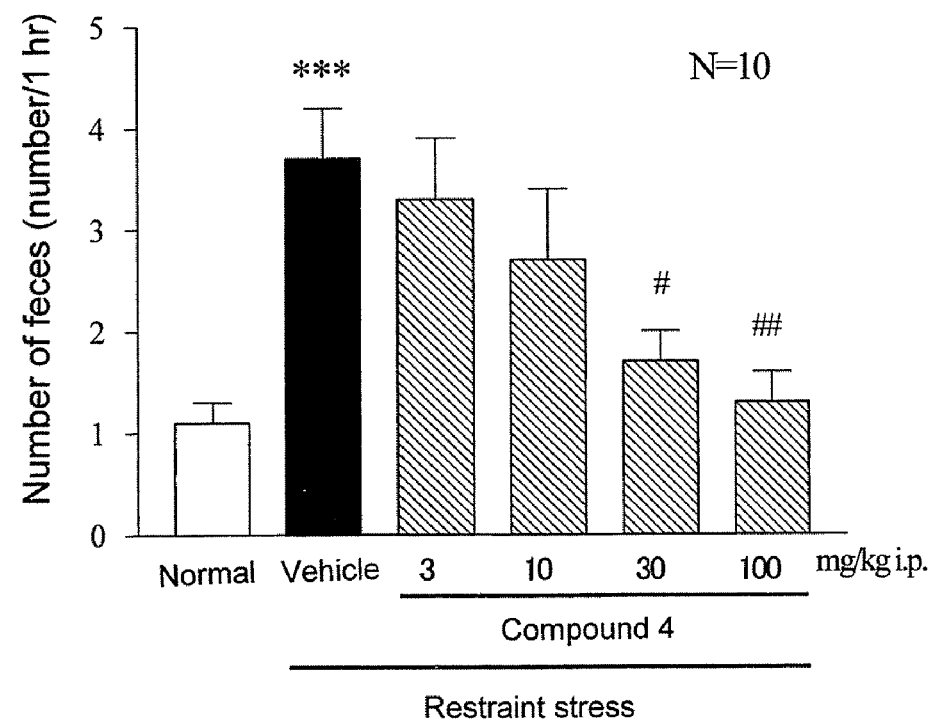

[Fig. 7]
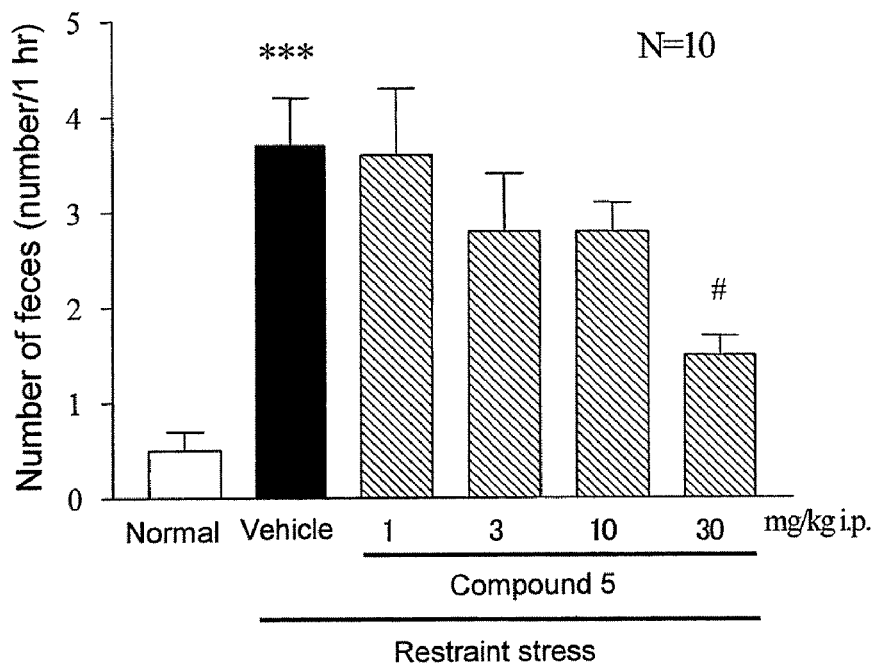
[Fig. 8]
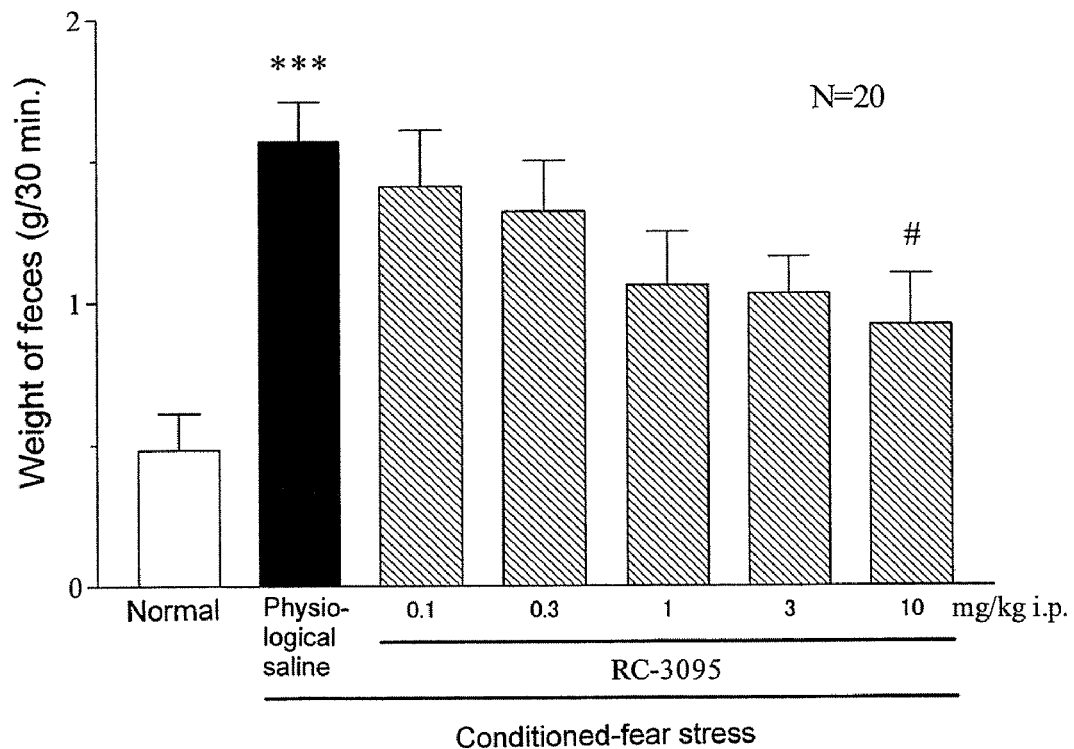

[Fig. 9]
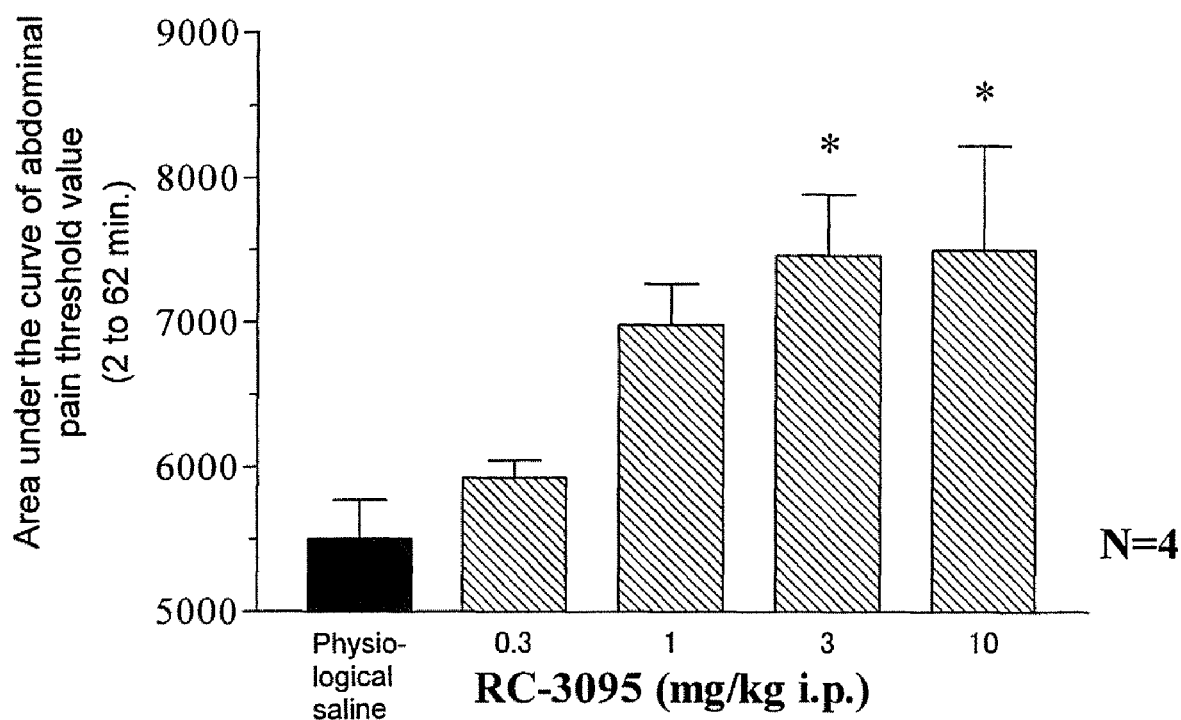

THERAPEUTIC AGENT FOR IRRITABLE BOWEL SYNDROME

TECHNICAL FIELD

The present invention relates to a therapeutic agent for irritable bowel syndrome.

BACKGROUND OF THE INVENTION

Irritable bowel syndrome (IBS) is a syndrome which causes chronic symptoms (e.g., abdominal pain, feeling of fullness and the like), bowel movement disorders (diarrhea, constipation and the like), defecation-trouble, straining and the like, due to functional abnormality of lower digestive tracts, mainly the large intestine, despite of the absence of organic disorders such as inflammation, tumor and the like, and is classified based on the conditions of bowel movement into diarrhea-predominant IBS, constipation-predominant IBS and alternating IBS which alternately repeats diarrhea and constipation. IBS is a disease which has a relatively high frequency occupying from 20 to 50% of bowel disease patients who take medical advices by visiting hospitals, is predominant in female because its male to female ratio is 1:2 regardless of the human race, and has high prevalence rate in the younger generation. Since mental stress is strongly concerned in its morbid states, it is regarded as a stress somatic disease and it is said that stress management is important for the improvement of symptoms. Actually, it is known that abnormal digestive tract movements are significantly accelerated and symptoms are worsen when an emotional stress is applied to IBS patients. In addition, since the symptoms continue, it is apt to form a vicious circle in which anxiety is increased in the patients so that the symptoms further worsen.

As the drug therapy of IBS, an anticholinergic is used for abdominal pain, and a tricyclic antidepressant for the improvement of pain threshold value reduction in digestive tracts, and an anti-diarrheal drug, a drug for controlling intestinal function and the like in the case of diarrhea and a saline cathartic and the like in the case of constipation for the improvement of bowel movement disorders, but these are merely a replacement therapy and their effects are not clear too. There is polycarbophil calcium as an agent from which effects can be expected for both diarrhea and constipation, which adjusts hardness of feces by becoming a gel in the intestines, but exerts very limited effects because not only there is a feeling of fullness at the initial stage of its administration but also it requires time for expressing the effects. Anxiolytics and antidepressants are used when anxiety and tension are considerably increased due to stress, but they are administered at a dose lower than the dose in the psychiatric region, so that there is a case in which the mental symptoms are not improved or a case in which these are improved but they do not show their effects on bowel movement disorder. Anxiolytics are effective for diarrhea and abdominal pain in some cases, generally among the symptoms of IBS, but there is a tendency that their effect on constipation is hardly expressed.

There are a 5-HT3 receptor antagonist alosetron and a 5-HT4 receptor agonist tegaserod as agents which have been drawing attention in recent years, and they are used in the diarrhea-predominant and constipation-predominant respectively. These agents improve bowel movement by regulating movement of intestines, and the expression of effect is quick. However, though alosetron shows a relatively high improving rate of from 40 to 60% for abdominal symptoms and diarrhea, constipation occurs in 30 to 35% of the patients and it causes ischemic colitis (including mortal cases) as a serious side effect, so that its use is limited (Non-patent Reference 1). In addition, it cannot be said that the effect of tegaserod on the constipation-predominant is sufficient, and there is a possibility of causing tachyphylaxis (a phenomenon in which resistance is generated when an agent is repeatedly administered within a short period of time).

By the way, when the living body receives a stress, it generates a hypothalamic-pituitary-adrenal system (HPA system) reaction in which adrenocorticotropic hormone (ACTH) is released through the secretion of a stress-related substance from the hypothalamus and subsequent action upon the anterior hypophysis, and the ACTH released into blood secretes corticosterone, and thereby shows various stress responses such as blood pressure increase and the like. As the stress-related substance, corticotrophin releasing hormone (CRH), bombesin (BB)/gastrin releasing peptide (GRP), vasopressin, neuropeptide Y, substance P, neurotensin and the like are known. Secretion of these substances from the hypothalamus is accelerated when a stress is applied to animals. Particularly regarding the CRH, it has been reported that it reinforces ACTH release and large bowel movement when administered to IBS patients (Non-patent Reference 2).

The bombesin/GRP as one of the stress-related substances is a brain-gut peptide and expresses various physiological actions via bombesin receptor. The bombesin receptor is classified into 3 subtypes of BB1, BB2 and BB3/BRS3 (bombesin receptor subtype-3), and as intrinsic ligands of mammals for BB1 and BB2 receptors, neuromedin B and GRP have been identified respectively. It has been reported that GRP and BB2 receptors are present ubiquitously in the brain, digestive tracts and the like, but GRP is markedly increased in amygdala and hypothalamus when a stress is applied to an animal (Non-patent Reference 3). In addition, it has been reported also that a BB2 receptor antagonist inhibits increase of ACTH when administered into the cerebral ventricle in a restraint stress-added rat (Non-patent Reference 4), but there are no reports on the concern of peripheral GRP and BB2 receptor in stress reactions.

As the role of the GRP/BB2 receptor in the digestive tract functions, it has been reported that it enhances the contraction in isolated human and rabbit ileum longitudinal muscle specimens (Non-patent References 5 and 6), and enhances the water secretion in guinea pigs in the coexistence of vasoactive intestinal peptide (VIP) (Non-patent Reference 7). However, there are no reports on its action on defication and its examination using a BB2 receptor antagonist.

As the BB2 receptor antagonist, a peptide compound (RC-3095) represented by the formula (I) is known (Non-patent Reference 8 and Patent reference 1).

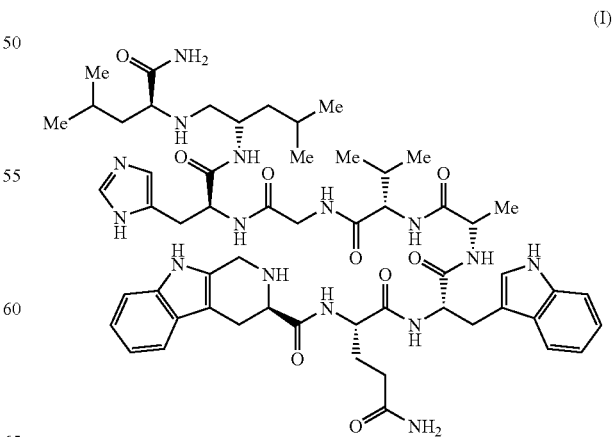

(I)

[In the Formula, Me Means Methyl.]

Since the bombesin/GRP also has a function as a cell growth factor and expression of the GRP/BB2 receptor is increased in various cancer cells of lung cancer, prostate cancer and the like, efficacy of RC-3095 has been reported by a large number of antitumor tests (Non-patent References 9 to 11). Currently, clinical tests of RC-3095 are carried out on various solid carcinomas, but there are no reports on the action of this compound upon the digestive tract functions, and there are no reports also on the efficacy and applicability of BB2 receptor antagonist for IBS.

As other BB2 receptor antagonists, for example, a compound represented by a formula (II) (BIM 26226, Non-patent Reference 12 and Patent Reference 2),

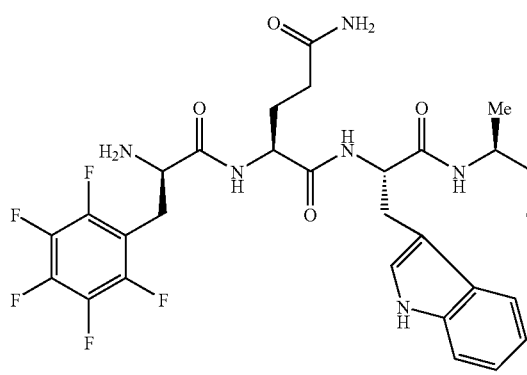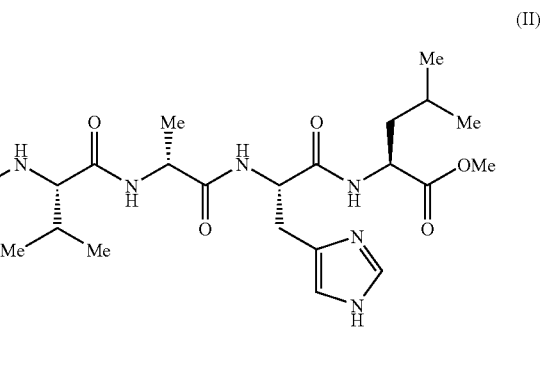

(II)

[In the Formula, Me Means Methyl]

1-ethyl-3-[methylene-(3',5'-di-tert-butyl-4'-hydroxyphenyl)]-5-(2'-carboxybenzyloxy)oxyindole (CP-70030; Non-patent Reference 13 and Patent Reference 2), 1-(3',4'-dichlorobenzyl)-5-bromo-spiro-[imidazoline-4,3'-azaindoline]-2, 2',5-trione (CP-75998; Non-patent Reference 13 and Patent Reference 2), (S)-3-(1H-indol-3-yl)-N-[1-(5-methoxypyridin-2-yl)cyclohexylmethyl]-2-methyl-2-[3-(4-nitrophenyl)ureido]propionamide (PD 176252; Non-patent Reference 14 and Patent Reference 3) and the compounds described in Patent References 1 to 8 and the like have been reported. However, efficacy and applicability of BB2 receptor antagonist for IBS are not reported also in these references.

Also, (2E)-3-[5-(4-nitrophenyl)-2-furyl]-1-phenyl-2-propen-1-one (CAS Registry No. 38898-76-9; Non-patent Reference 15) has been reported as an intermediate for synthesizing a compound having an antibacterial action, but its BB2 receptor antagonism and efficacy and applicability for IBS are not reported therein.

In addition, 2-chloro-5-nitro-N-(4-{[2-(pyridin-3-yl)piperidin-1-yl]sulfonyl}phenyl)benzamide (CAS Registry No. 393834-75-8), N-(4-chloro-2-methylphenyl)-2-[(3,4-dimethoxyphenyl)phenylsulfonyl]amino]acetamide (CAS Registry No. 335208-47-4), and N-[3-(1,3-benzothiazol-2-yl)-6-isopropyl-4,5,6,7-tetrahydrothieno[2,3-c]pyridin-2-yl]-3,5-dimethoxybenzamide (CAS Registry No. 486396-92-3) are known as catalog compounds, but their BB2 receptor antagonism and efficacy and applicability for IBS have not been reported.

Non-patent Reference 1: *American Journal of Gastroenterology*, (USA), 2003, vol. 98, p. 750-758
Non-patent Reference 2: *Gut*, (England), 1998, vol. 42, p. 845-849
Non-patent Reference 3: *The Journal of Neuroscience*, (USA), 1998, vol. 18, p. 4758-4766
Non-patent Reference 4: *Life Sciences*, (Holland), 2002, vol. 70, p. 2953-2966
Non-patent Reference 5: *Gastroenterology*, (USA), 1991, vol. 100, p. 980-985
Non-patent Reference 6: *Neurogastroenterology and Motility*, (England), 1997, vol. 9, p. 265-270
Non-patent Reference 7: *Annals of the New York Academy of Science*, (USA), 2000, vol. 921, p. 420-424
Non-patent Reference 8: *The Prostate*, (USA), 1994, vol. 25, p. 29-38
Non-patent Reference 9: *Cancer*, (USA), 1998, vol. 83, p. 1335-1343
Non-patent Reference 10: *British Journal of Cancer*, 2000, vol. 83, p. 906-913
Non-patent Reference 11: *Cancer*, (USA), 2000, vol. 88, p. 1384-1392
Non-patent Reference 12: *Regulatory Peptide*, (Holland), 1994, vol. 53, p. 165-173
Non-patent Reference 13: *Bioorganic & Medicinal Chemistry Letters*, (Holland), 1992, vol. 2. p. 333-338
Non-patent Reference 14: *Bioorganic & Medicinal Chemistry Letters*, (Holland), 1998, vol. 8, p. 2589-2594
Non-patent Reference 15: *Il Farmaco*, (Holland), 2001, vol. 56, no. 10, p. 919-927
Patent Reference 1: International Publication No. 92/09626
Patent Reference 2: International Publication No. 91/9102746
Patent Reference 3: International Publication No. 92/07830
Patent Reference 4: International Publication No. 98/07718
Patent Reference 5: JP-A-7-258081
Patent Reference 6: International Publication No. 00/09115
Patent Reference 7: International Publication No. 02/40469
Patent Reference 8: International Publication No. 02/40475

DISCLOSURE OF THE INVENTION

Problems that the Invention is to Solve

Since the conventional therapeutic agents for IBS do not show sufficient efficacy for both an abdominal symptom and bowel movement disorder and cannot be sufficiently satisfactory from the viewpoint of safety as described in the foregoing, great demand has been directed toward the provision of a therapeutic agent for IBS excellent in efficacy and safety.

Means for Solving the Problems

Under such a situation, the present inventors have conducted extensive studies with the aim of providing a therapeutic agent for IBS which shows excellent efficacy in both an abdominal symptom and bowel movement disorder. As a result, it was found unexpectedly that BB2 receptor antagonists including RC-3095 are effective for bowel movement disorder in a stress-induced defication model. As a result of further carrying out extensive studies, it was found that RC-3095 is effective for an abdominal symptom in an abdominal pain model by large intestinal distension using abdominal muscle contraction reaction as the index, and that RC-3095 is a therapeutic agent for IBS which shows excellent efficacy for both an abdominal symptom and bowel movement disorder, thus accomplishing the present invention.

That is, according to the present invention, there are provided:

(1) a therapeutic agent for irritable bowel syndrome (IBS), which comprises a bombesin type 2 (BB2) receptor antagonist as an active ingredient,
(2) the therapeutic agent described in (1), wherein the aforementioned IBS is diarrhea-predominant IBS,
(3) the therapeutic agent described in (1), wherein the aforementioned IBS is alternating IBS,
(4) the therapeutic agent described in (1), wherein the aforementioned IBS is constipation-predominant IBS,
(5) the therapeutic agent described in any one of (1) to (4), wherein the BB2 receptor antagonist is a compound selected from the group consisting of
a compound represented by a formula (I)

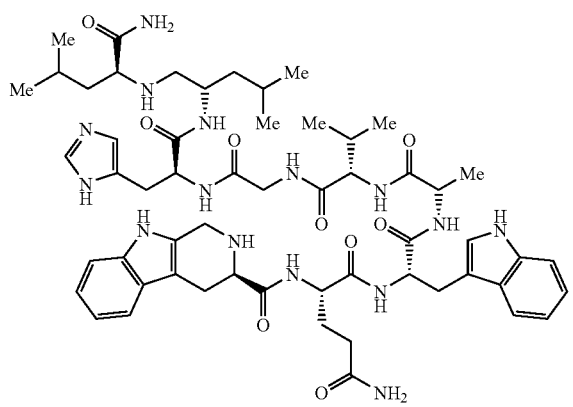

(I)

[In the Formula, Me Means Methyl],
a compound represented by a formula (II)

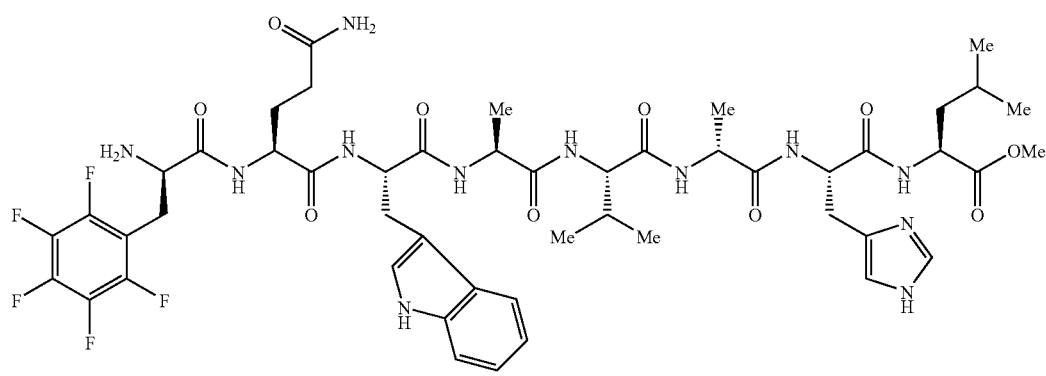

(II)

[In the Formula, Me Means Methyl],
1-ethyl-3-[methylene-(3',5'-di-tert-butyl-4'-hydroxyphenyl)]-5-(2'-carboxybenzyloxy)oxyindole,
1-(3',4'-dichlorobenzyl)-5-bromo-spiro-[imidazoline-4,3'-azaindoline]-2,2',5-trione,
(S)-3-(1H-indol-3-yl)-N-[1-(5-methoxypyridin-2-yl)cyclohexylmethyl]-2-methyl-2-[3-(4-nitrophenyl)ureido]propionamide,
2-[4-(1-naphthyl)-5-phenyl-1,3-thiazol-2-yl]pyridine,
(2E)-3-[5-(4-nitrophenyl)-2-furyl]-1-phenyl-2-propen-1-one,
2-chloro-5-nitro-N-(4-{[2-(pyridin-3-yl)piperidin-1-yl]sulfonyl}phenyl)benzamide,
N-(4-chloro-2-methylphenyl)-2-[(3,4-dimethoxyphenyl)phenylsulfonyl]amino]acetamide, and
N-[3-(1,3-benzothiazol-2-yl)-6-isopropyl-4,5,6,7-tetrahydrothieno[2,3-c]pyridin-2-yl]-3,5-dimethoxybenzamide,
or a pharmaceutically acceptable salt thereof,
(6) use of a BB2 receptor antagonist for treating IBS,
(7) use of a BB2 receptor antagonist for the manufacture of a therapeutic agent for IBS,
(8) the use described in (6) to (7), wherein the aforementioned IBS is diarrhea-predominant IBS,
(9) the use described in 6) or (7), wherein the aforementioned IBS is alternating IBS,
(10) the use described in (6) or (7), wherein the aforementioned IBS is constipation-predominant IBS,
(11) the use described in any one of (6) to (10), wherein the BB2 receptor antagonist is a compound selected from the group consisting of
the compound of formula (I) described in (5),
the compound of formula (II) described in (5),
1-ethyl-3-[methylene-(3',5'-di-tert-butyl-4'-hydroxyphenyl)]-5-(2'-carboxybenzyloxy)oxyindole,
1-(3',4'-dichlorobenzyl)-5-bromo-spiro-[imidazoline-4,3'-azaindoline]-2,2',5-trione,
(S)-3-(1H-indol-3-yl)-N-[1-(5-methoxypyridin-2-yl)cyclohexylmethyl]-2-methyl-2-[3-(4-nitrophenyl)ureido]propionamide,
2-[4-(1-naphthyl)-5-phenyl-1,3-thiazol-2-yl]pyridine,
(2E)-3-[5-(4-nitrophenyl)-2-furyl]-1-phenyl-2-propen-1-one,
2-chloro-5-nitro-N-(4-{[2-(pyridin-3-yl)piperidin-1-yl]sulfonyl}phenyl)benzamide,
N-(4-chloro-2-methylphenyl)-2-[(3,4-dimethoxyphenyl)phenylsulfonyl]amino]acetamide, and
N-[3-(1,3-benzothiazol-2-yl)-6-isopropyl-4,5,6,7-tetrahydrothieno[2,3-c]pyridin-2-yl]-3,5-dimethoxybenzamide,
or a pharmaceutically acceptable salt thereof,
(12) a method for treating IBS, which comprises administering an effective amount of a BB2 receptor antagonist to a patient,

(13) the method described in (12), wherein the aforementioned IBS is diarrhea-predominant IBS,
(14) the method described in (12), wherein the aforementioned IBS is alternating IBS,
(15) the method described in (12), wherein the aforementioned IBS is constipation-predominant IBS, and
(16) the method described in any one of (12) to (15), wherein the BB2 receptor antagonist is a compound selected from the group consisting of
the compound of formula (I) described in (5),
the compound of formula (II) described in (5),
1-ethyl-3-[methylene-(3',5'-di-tert-butyl-4'-hydroxyphenyl)]-5-(2'-carboxybenzyloxy)oxyindole,
1-(3',4'-dichlorobenzyl)-5-bromo-spiro-[imidazoline-4,3'-azaindoline]-2,2',5-trione,
(S)-3-(1H-indol-3-yl)-N-[1-(5-methoxypyridin-2-yl)cyclohexylmethyl]-2-methyl-2-[3-(4-nitrophenyl)ureido]propionamide,
2-[4-(1-naphthyl)-5-phenyl-1,3-thiazol-2-yl]pyridine,
(2E)-3-[5-(4-nitrophenyl)-2-furyl]-1-phenyl-2-propen-1-one,
2-chloro-5-nitro-N-(4-{[2-(pyridin-3-yl)piperidin-1-yl]sulfonyl}phenyl)benzamide,
N-(4-chloro-2-methylphenyl)-2-[(3,4-dimethoxyphenyl)phenylsulfonyl]amino]acetamide, and
N-[3-(1,3-benzothiazol-2-yl)-6-isopropyl-4,5,6,7-tetrahydrothieno[2,3-c]pyridin-2-yl]-3,5-dimethoxybenzamide,
or a pharmaceutically acceptable salt thereof.

Effect of the Invention

The therapeutic agent for IBS of the present invention exerts excellent IBS-treating effect by antagonizing the BB2 receptor. The therapeutic agent for IBS of the present invention is useful as a therapeutic agent for TBS having high efficacy because it shows its efficacy in both an abdominal symptom and bowel movement disorder, whereas the conventional therapeutic agents for IBS do not show sufficient efficacy in both an abdominal symptom and bowel movement disorder.

BRIEF DESCRIPTION OF THE DRAWINGS

FIG. 1 shows a result of the GRP concentration in blood plasma in Example 2.
FIG. 2 shows a result of the RC-3095-administration group in Example 3.
FIG. 3 shows a result of the 2-[4-(1-naphthyl)-5-phenyl-1,3-thiazol-2-yl]pyridine (compound 1)-administration group in Example 3.
FIG. 4 shows a result of the (2E)-3-[5-(4-nitrophenyl)-2-furyl]-1-phenyl-2-propen-1-one (compound 2) -administration group in Example 3.
FIG. 5 shows a result of the 2-chloro-5-nitro-N-(4-{[2-(pyridin-3-yl)piperidin-1-yl]sulfonyl}phenyl)benzamide (compound 3)-administration group in Example 3.
FIG. 6 shows a result of the N-(4-chloro-2-methylphenyl)-2-[(3,4-dimethoxyphenyl)phenylsulfonyl]amino]acetamide (compound 4)-administration group in Example 3.
FIG. 7 shows a result of the N-[3-(1,3-benzothiazol-2-yl)-6-isopropyl-4,5,6,7-tetrahydrothieno[2,3-c]pyridin-2-yl]-3,5-dimethoxybenzamide hydrochloride (compound 5)-administration group in Example 3.
FIG. 8 shows a result of the RC-3095-administration group in Example 4.
FIG. 9 shows a result of the RC-3095-administration group in Example 5.

BEST MODE FOR CARRYING OUT THE INVENTION

The following describes the present invention in detail.
According to this description, the "irritable bowel syndrome" (to be referred to as "IBS" hereinafter) includes diarrhea-predominant IBS, constipation-predominant IBS and alternating IBS. Preferred as the indication of the therapeutic agent of the present invention is diarrhea-predominant IBS or alternating IBS, particularly preferred is diarrhea-predominant IBS.
The "bowel movement disorder" means constipation and/or diarrhea.
The "abdominal symptom" means an abdominal pain, a feeling of fullness and/or abdominal uncomfortable feeling.
The "BB2 receptor antagonist" is a compound which inhibits a BB2 receptor-mediated action by competitively acting with an agonist GRP. Such a BB2 receptor antagonist is not particularly limited with the proviso that it is a compound which has a therapeutic effect on a symptom of IBS, such as a bowel movement disorder and/or abdominal symptom. Preferred is a compound which has a therapeutic effect on both of a bowel movement disorder and abdominal symptom. In addition, preferred as another embodiment is a compound having, as a BB2 receptor antagonistic activity by the test method described in Example 1 which is described later, a 50% binding inhibition concentration of 10 µM or less, more preferred is a compound having that of 3 µM or less, further preferred is a compound having that of 1 µM or less. For example, RC-3095, BIM 26226, CP-70030, CP-75998, PD 176252 and pharmaceutically acceptable salts thereof, the BB2 receptor antagonists disclosed in the aforementioned Patent References 1 to 8 and compounds 1 to 5 and the like can be illustratively cited, of which RC-3095 and compounds 1 to 5 are preferable and RC-3095 is more preferable. These BB2 receptor antagonists can be purchased or easily obtained by conventionally known methods, the methods described in the production examples which are described later or the methods which are obvious to those skilled in the art. In addition, the present invention includes a therapeutic agent which concomitantly use one or two or more of these BB2 receptor antagonists.
The aforementioned BB2 receptor antagonists form acid addition salts or salts with bases in some cases, and such salts are included in the present invention with the proviso that they are pharmaceutically acceptable salts. Illustratively, acid addition salts with inorganic acids (e.g., hydrochloric acid, hydrobromic acid, hydriodic acid, sulfuric acid, nitric acid, phosphoric acid and the like) or with organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like), salts with inorganic bases (e.g., sodium, potassium, magnesium, calcium, aluminum and the like), or with organic bases (e.g., methylamine, ethylamine, ethanolamine, lysine, ornithine and the like), ammonium salts and the like can be cited. In addition, the aforementioned BB2 receptor antagonists or their pharmaceutically acceptable salts may be various hydrates or solvates, and their polymorphic substances are also included. These pharmaceutically acceptable salts of BB2 receptor antagonists can be easily produced by the salt formation methods which are generally employed by those skilled in the art.

Also, mixtures and isolated substances of various stereoisomers such as geometrical isomers, tautomers, optical isomers and the like are included in the aforementioned BB2 receptor antagonists. These isomers can be isolated and purified by conventionally known methods, for example, extraction, precipitation, fractional chromatography, fractional crystallization, recrystallization and the like. In addition, optical isomers can be resolved by usual methods such as a fractional crystallization in which they are recrystallized from appropriate salts, a chromatography and the like.

In addition, pharmacologically acceptable prodrugs are also included in the aforementioned BB2 receptor antagonists. A pharmacologically acceptable prodrug is a compound which is converted into a BB2 receptor antagonist by solvolysis or under a physiological condition. As the groups which form prodrugs, the groups described in "Progress in Medicine" 1985, vol. 5, p. 2157-2161 and "Iyakuhin no Kaihatsu (Development of Medicines)", Hirokawa Shoten, 1990, vol. 7, Bunshi Sekkei (Molecular Design), p. 163-198 can be exemplified. These prodrugs of BB2 receptor antagonists can be easily produced by the methods which can be generally employed by those skilled in the art.

The pharmaceutical preparations which comprise a BB2 receptor antagonist as an active ingredient can be prepared by using carriers, fillers and other additive agents which are generally used in the preparation of medicines.

The administration may be either oral administration by tablets, pills, capsules, granules, powders, solutions and the like or parenteral administration by injections for intravenous injection, intramuscular injection and the like, suppositories, transdermal agents, transnasal agents, inhalations and the like. The dose is optionally determined in response to individual case by taking symptoms, age and sex of the object to be administered and the like into consideration, but in general, it is approximately from 0.001 mg/kg to 100 mg/kg per day per adult in the case of oral administration, and this is administered at once or by dividing into 2 to 4 doses. Also, when intravenously administered due to the symptom, it is administered once or two or more times per day, within the range of generally from 0.0001 mg/kg to 10 mg/kg per once per adult. In addition, in the case of inhalation, it is administered once or two or more times per day, within the range of generally from 0.0001 mg/kg to 1 mg/kg per once per adult.

As the solid composition for oral administration by the present invention, tablets, powders, granules and the like are used. In such a solid composition, one or more active substances are mixed with at least one inert filler such as lactose, mannitol, glucose, hydroxypropylcellulose, microcrystalline cellulose, starch, polyvinyl pyrrolidone, aluminum magnesium silicate or the like. In accordance with the usual way, the composition may contain inert additives such as lubricants (e.g., magnesium stearate and the like), disintegrators (e.g., carboxymethylstarch sodium and the like), solubilizing agents and solubilization assisting agents. As occasion demands, the tablets or pills may be coated with a sugar coating or a gastric or enteric coating.

As the liquid composition for oral administration, pharmaceutically acceptable emulsions, solutions, suspensions, syrups, elixirs and the like are included, and generally used inert solvents such as purified water, ethanol and the like can be used. In addition to the inert solvents, this composition may contain auxiliary agents (e.g., solubilizing agents, moistening agents, suspending agents and the like), sweeteners, correctives, aromatics and antiseptics.

As the injections for parenteral administration, sterile aqueous or non-aqueous solutions, suspensions and emulsions are included. As the aqueous solvent, for example, distilled water for injection and physiological saline are included. Examples of the non-aqueous solvent include propylene glycol, polyethylene glycol, plant oil (e.g., olive oil or the like), alcohols (e.g., ethanol or the like), polysorbate 80 (trade name) and the like. Such a composition may further contain tonicity agents, antiseptics, moistening agents, emulsifying agents, dispersing agents, stabilizing agents, solubilizing agents and solubilization assisting agents. These are sterilized by, for example, filtration through a bacteria retaining filter, formulation of bactericides or irradiation. In addition, these can also be used by producing sterile solid compositions and dissolving or suspending them in sterile water or a sterile solvent for injection prior to use.

Inhalations, transmucosal agents (e.g., transnasal agents and the like) are used in the form of solid, liquid or semisolid, and can be produced in accordance with the conventionally known methods. For example, excipients (e.g., lactose, starch and the like) and also pH adjusting agents, antiseptics, surfactants, lubricants, stabilizers, thickeners and the like may be optionally added. An appropriate device for inhalation or blowing can be used for the administration. For example, a compound can be administered as such or as a powder of formulated mixture, or as a solution or suspension in combination with a medically acceptable carrier, by using conventionally known device or a sprayer (e.g., a measured administration inhalation device or the like). The dry powder inhaler or the like may be for single or multiple administration use, and a dry powder or powder-containing capsule can be used. Alternatively, it may be in the form of a pressurized aerosol spray or the like which uses an appropriate propellant such as suitable gas (e.g., chlorofluoroalkane, hydrofluoroalkane, carbon dioxide or the like).

EXAMPLES

The following illustratively describes the present invention based on examples, but these do not limit the scope of the present invention.
(Test Methods)

Example 1

BB2 Receptor Antagonistic Activity

A BB2 receptor binding test was carried out using a membrane sample prepared from a human prostate cancer-derived PC-3 cell. The PC-3 cell was cultured using RPMI-1640 medium containing 5% fetal bovine serum, and then a membrane sample was prepared by the following methods. The cells loosened by a trypsin treatment were mixed with 50 mM Tris-HCl buffer (pH 7.4, containing 0.2 mg/ml trypsin inhibitor and 0.2 mg/ml benzamidine) and homogenized by Polytron. The cell suspension was centrifuged at 1,500 rpm for 10 minutes, and the thus obtained supernatant was subjected to 1 hour of ultracentrifugation at 37,000 rpm. The precipitate was suspended in the aforementioned buffer to a concentration of 0.4 mg protein/ml and stored at −80° C.

The BB2 receptor binding test was carried out by the following method, and the receptor antagonistic activity of a compound to be tested was calculated. A 50 µl portion of the membrane sample, 50 µl of an assay buffer (20 mM HEPES-HBSS containing 0.1% bovine serum albumin and 0.1 mg/ml bacitracin, pH 7.4) $^{125}$I [Tyr$^4$] bombesin (0.075 nM) and 2 µl of each compound to be tested dissolved in dimethyl sulfoxide were added to a 96 well assay plate and incubated at room temperature for 2 hours. Non-specific binding was measured using 1 µM of bombesin. After completion of the incubation, the reaction liquid was filtered through a Whatman GF/B filter which had been soaked in 0.5% polyethyleneimine. The radioactivity on the filter was measured using a microplate scintillation counter (Top Count, Perkin-Elmer). As a result, 50% binding inhibition concentration of RC-3095, compound 1, compound 2, compound 3, compound 4 and compound 5 was 20, 504, 1330, 342, 398 and 383 nM, respectively.

Example 2

Measurement of Plasma GRP Concentration

In order to measure plasma GRP concentration at the time of loading a restraint stress, fed male ddY mice were put into a restraint stress cage (KN-469, Natsume Seisakusho), and blood samples were collected by decapitation 5, 10, 15, 30, 45, 60, 90, 120 and 180 minutes after the commencement of restriction. Plasma was obtained by centrifuging blood at 3,000 rpm for 15 minutes. The plasma GRP concentration was measured using Gastrin Releasing Peptide (GRP) EIA Kit (SCETI Co., Ltd).

As a result, as shown in FIG. 1, it was shown that plasma concentration of GRP as an intrinsic ligand of BB2 receptor increases by the restraint stress loading. Based on this, it was able to confirm that the GRP released at the peripheral at the time of stress loading is concerned in the morbid states of IBS.

Example 3

Restraint Stress-Induced Defication Model

RC-3095 was used by dissolving in physiological saline, and compound 1, compound 3 and compound 5 in physiological saline containing 5% ethanol+5% Cremophor, and compound 2 and compound 4 in water for injection containing 20% propylene glycol+20% Tween 80. Just after intraperitoneal administration of a compound to be tested to each of fed male ddY mice, the animal was put into a restraint stress cage (KN-469, Natsume Seisakusho). The number of feces excreted during a period of from the restriction commencement to 1 hour thereafter was measured. Normal group was put into a separate cage, and number of feces excreted during 1 hour was measured in the same manner.

As a result, as shown in FIG. 2, RC-3095 showed a dose-dependent inhibitory effect on the defication, and its 50% inhibition dose was 5.2 mg/kg. Also, the compound 1 showed about 83% of inhibitory effect on the defication at 10 mg/kg (FIG. 3). In addition, 50% inhibition dose for restraint stress-induced defication of the compound 2, compound 3, compound 4 and compound 5 was 34.3, 19.0, 13.5 and 15.6 mg/kg, respectively (FIGS. 4 to 7). Based on this, it was able to confirm that the BB2 receptor antagonists show the action to improve the bowel movement symptom of diarrhea-predominant IBS.

Example 4

Conditioned-Fear Stress (CFS)—Induced Defication Model

Fed male Sprague-Dawley rats were used. The rats were put into an electric shock device having a grid set in the floor (17×17×39 cm, trade name: CB 2000 type, O'Hara), and conditioning was carried out after 3 seconds of a warning sound, by applying an electric current of 2.5 mA for 5 seconds per once per minute, a total of 15 times, and carrying out light irradiation by three 40 W electric bulbs at the time of the electric shock. The normal group was put into the measuring device by the same protocol, but the electric shock was not applied. After about 24 hours, the rats were again put into the electric shock device just after intraperitoneal administration of tested compound, and CFS loading was carried out by applying 3 seconds of warning sound and 5 seconds light irradiation for 30 minutes. Wet weights of excreted feces were measured for 30 minutes starting from the commencement of CFS loading. In this connection, the feces just after putting of the rats into the measuring device were excluded from measured values.

As a result, as shown in FIG. 8, RC-3095 showed a dose-dependent inhibitory effect on the defication and showed significant inhibitory action at a dose of 10 mg/kg. Based on this, it was able to confirm that the BB2 receptor antagonists show the action to improve the bowel movement symptom of diarrhea-predominant IBS.

Example 5

Abdominal Pain Model by Large Intestinal Distension Using Abdominal Muscle Contraction Reaction as the Index Fed male Wistar rats were used. Under pentobarbital anesthesia, an electrode for electromyogram use (trade name: M-1.5I, Star Medical) was sewed on the outer abdominal oblique muscle. The electrode cord was fished out from the body of around the back of the head through the skin and protected with a protective jacket prepared by processing Velcro. The test was carried out when 5 days or more passed after the surgical operation.

On the day of the test, a latex balloon of 5 to 6 cm in length was inserted from the rat anus under a light ether anesthesia and adjusted such that the balloon end is positioned at 2 cm from the anus. The catheter continuing from the balloon was fixed to the tail base with a tape and connected to a pressure transducer and a plastic bottle filled with water via a three-way cock. The plastic bottle was connected to a motor-aided device such that its height can be increased at a constant rate, and the colon-rectum was distended by increasing height of the plastic bottle. The balloon internal pressure signal was amplified using an amplifier for strain pressure use. After recovering from the ether anesthesia in a cage (23.5×19×19 cm), the colon-rectum distension was carried out. When the colon-rectum distension pressure is continuously increased from 0 mmHg, the rat takes an action to shrink the belly due to abdominal pain at a certain point of time. As a result, the abdominal muscle contracts and the electromyogram activities increase suddenly and sharply. The pressure at this point of time was regarded as the abdominal pain reflection threshold value. The electromyogram activities were amplified using an amplifier for bioelectric use (trade name: AB-621G, Nihon Kohden Corp.), and recorded by a data recording interface (trade name: 1401 plus, Cambridge Electronic Design, Cambridge, England). The colon-rectum distension was repeatedly carried out at intervals of 4 minutes until completion of the test. The compound was administered 2 minutes after completion of the measurement of the pre-administration value, and the colon-rectum distension was repeated until 60 minutes after the administration. By regarding the threshold value before the compound administration as 100%, area under curve (AUC) of threshold values until 60 minutes after the administration was calculated.

As a result, as shown in FIG. 9, RC-3095 showed the action to dose-dependently increase abdominal pain threshold value and showed significant increasing action at a dose of 3 and 10 mg/kg. Based on this, it was able to confirm that the BB2 receptor antagonist has the action to improve abdominal pain.

PRODUCTION EXAMPLES

The following shows production examples of the compounds concerned in the active ingredient of the therapeutic agent of the present invention. In this connection, the compound 1 is a novel substance. In addition, since novel substances are included in the material compounds to be used in the production examples, production methods of such compounds are described as reference production examples.

Reference Production Example 1

A 842 mg portion of 4-(acetylamino)benzene sulfonyl chloride was added under ice-cooling to a pyridine solution (10 ml) of 3-(piperidin-2-yl)pyridine and stirred at room temperature for 2 hours. The solvent was concentrated under a reduced pressure, and the thus obtained residue was mixed with ethyl acetate and then washed with water, 1 M hydrochloric acid and saturated brine. This was dried with anhydrous sodium sulfate and then concentrated under a reduced pressure, and the thus obtained residue was purified by a silica gel column chromatography using chloroform:methanol (98:2) as the elution solvent, thereby obtaining 1.00 g of N-(4-{[2-(pyridin-3-yl)piperidin-1-yl]sulfonyl}phenyl)acetamide as a yellow foamy substance. FAB-MS (Pos): 360 $[M+H]^+$.

Reference Production Example 2

A 1.81 ml portion of methanesulfonic acid was added to a methanol solution (10 ml) of 1.0 g N-(4-{[2-(pyridin-3-yl)piperidin-1-yl]sulfonyl}phenyl)acetamide and stirred overnight at room temperature. The reaction liquid was poured into ice water and neutralized with sodium bicarbonate, and then layer separation operation was carried out by adding ethyl acetate. The organic layer was washed with saturated sodium chloride aqueous solution, dried with anhydrous sodium sulfate and then concentrated under a reduced pressure to obtain 695 mg of 4-{[2-(pyridin-3-yl)piperidin-1-yl]sulfonyl}aniline as pale yellow crystals.
FAB-MS (Pos): 318 $[M+H]^+$.

Reference Production Example 3

Under ice-cooling, 296 mg of sodium hydride was added to an N,N-dimethylformamide solution (30 ml) of 1.99 g N-(3,4-dimethoxyphenyl)benzene sulfonamide and stirred at room temperature for 30 minutes, and then 0.75 ml of ethyl bromoacetate was added thereto and stirred for 2 hours. The reaction liquid was poured into ice water, acidified by adding 1 M hydrochloric acid and then extracted with ethyl acetate. The organic layer was washed with saturated brine, dried with anhydrous sodium sulfate and then concentrated under a reduced pressure. The thus obtained residue was purified by a silica gel column chromatography using ethyl acetate:n-hexane (1:2) as the elution solvent, thereby obtaining 2.47 g of ethyl [(3,4-dimethoxyphenyl)(phenylsulfonyl)amino]acetate as a pale yellow oily substance.
FAB-MS (Pos): 380 $[M+H]^+$.

Reference Production Example 4

A 20 ml portion of 1 M sodium hydroxide aqueous solution was added to a tetrahydrofuran solution (20 ml) of 2.48 g of ethyl [(3,4-dimethoxyphenyl)(phenylsulfonyl)amino]acetate and stirred at room temperature for 2 hours. This was acidified by adding 1 M hydrochloric acid and then layer separation operation was carried out by adding chloroform thereto, and the organic layer was washed with saturated brine, dried with anhydrous sodium sulfate and then concentrated under a reduced pressure to obtain 2.28 g of [(3,4-dimethoxyphenyl)(phenylsulfonyl)amino]acetic acid as a pale yellow foamy substance.
FAB-MS (Neg): 350 $[M-H]^-$.

Production Example 1

Compound 1

A 183 mg portion of pyridine-2-carbothioamide hydrochloride and 209 mg of calcium carbonate were added at room temperature to a 2-propanol solution (20 ml) of 340 mg of 2-bromo-1-(1-naphthyl)-2-phenylethanone and heated overnight under reflux. The reaction liquid was acidified by adding 1 M hydrochloric acid and then extracted with ethyl acetate. The organic layer was washed with saturated brine, dried with anhydrous sodium sulfate and then concentrated under a reduced pressure. The thus obtained residue was purified by a silica gel column chromatography using ethyl acetate:n-hexane (1:9) as the elution solvent, thereby obtaining 227 mg of 2-[4-(1-naphthyl)-5-phenyl-1,3-thiazol-2-yl]pyridine as a colorless solid.
FAB-MS (Pos): 365 $[M+H]^+$.

Production Example 2

Compound 3

A 220 mg portion of 2-chloro-5-nitrobenzoyl chloride was added to a pyridine solution (10 ml) of 318 mg of 4-{[2-(pyridin-3-yl)piperidin-1-yl]sulfonyl}aniline and stirred overnight at room temperature. After stirring at 50° C. for 4 hours, 220 mg of 2-chloro-5-nitrobenzoyl chloride was further added thereto and stirred at 50° C. for 2 hours. Ethyl acetate and water were added thereto to carry out layer separation operation, and the organic layer was washed with saturated sodium chloride aqueous solution. After drying with anhydrous sodium sulfate, this was concentrated under a reduced pressure and the thus obtained residue was purified by a silica gel column chromatography using chloroform:methanol (98:2) as the elution solvent, thereby obtaining 426 mg of 2-chloro-5-nitro-N-(4-{[2-(pyridin-3-yl)piperidin-1-yl]sulfonyl}phenyl)benzamide as colorless crystals.
FAB-MS (Pos): 501 $[M+H]^+$.

Production Example 3

Compound 4

A 142 mg portion of 4-chloro-2-methylaniline, 203 mg of 1-hydroxybenzotriazole and 288 mg of 1-ethyl-3-(3-dimethylaminopropyl)carbodiimide hydrochloride were added to a dichloromethane solution (10 ml) of 352 mg of [(3,4-dimethoxyphenyl)(phenylsulfonyl)amino]acetic acid and stirred overnight at room temperature. Chloroform and water were added thereto to carry out layer separation operation, and the organic layer was washed with saturated brine, dried with anhydrous sodium sulfate and then concentrated under a reduced pressure. The thus obtained residue was purified by a silica gel column chromatography using chloroform as the elution solvent, thereby obtaining 287 mg of N-(4-chloro-2-methylphenyl)-2-[(3,4-dimethoxyphenyl)phenylsulfonyl]amino]acetamide as colorless crystals.

FAB-MS (Neg): 473 [M−H]⁻.

Structural formulae of the compounds 1 to 5 are shown in the following Table 1.

In this connection, Me in the table means methyl. In addition, when HCl is described in the structural formula, it indicates that the compound is hydrochloride.

TABLE 1

| Compound No. | Structural formula |
|---|---|
| 1 | 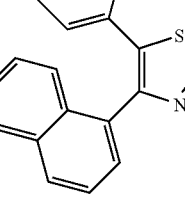 |
| 2 | 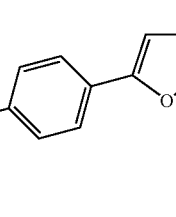 |
| 3 | 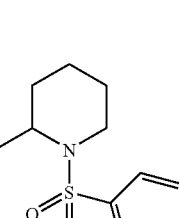 |
| 4 |  |

TABLE 1-continued

| Compound No. | Structural formula |
|---|---|
| 5 | 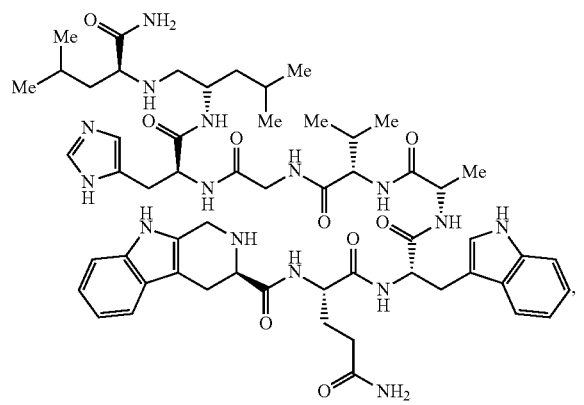 |

INDUSTRIAL APPLICABILITY

As has been described in the foregoing, it was shown that the BB2 receptor antagonists typified by RC-3095 are therapeutic agents for IBS, which show excellent efficacy in both of an abdominal symptom and bowel movement disorder. Thus, according to the present invention, it became possible to provide a therapeutic agent for IBS which comprises, as an active ingredient, a bombesin 2 (BB2) receptor antagonist exerting an excellent efficacy in both an abdominal symptom and bowel movement disorder.

The invention claimed is:

1. A method for treating Irritable Bowel Syndrome (IBS), which comprises administering an effective amount of a BB2 receptor antagonist to a patient with IBS.

2. The method described in claim 1, wherein the IBS is a diarrhea-predominant IBS.

3. The method described in claim 1, wherein the IBS is an alternating IBS.

4. The method described in claim 1, wherein the IBS is a constipation-predominant IBS.

5. The method described in any one of claims 1 to 4, wherein the BB2 receptor antagonist is selected from the group consisting of:

the compound of formula (I)

(I)

the compound of formula (II)

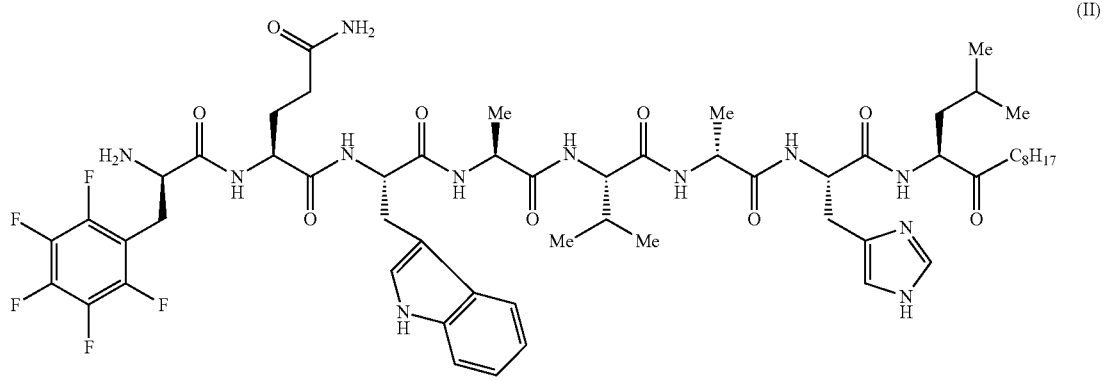

1-ethyl-3-[methylene-(3',5'-di-tert-butyl-4'-hydroxyphenyl)]-5-(2'-carboxybenzyloxy)oxyindole,
1-(3',4'-dichlorobenzyl)-5-bromo-spiro- [imidazoline-4,3'-azaindoline]-2,2',5-trione,
(S)-3-(1H-indol-3-yl)-N-[1-(5-methoxypyridin-2-yl)cyclohexylmethyl]-2-methyl-2-[3-(4-nitrophenyl)ureido]propionamide,
2-[4-(1-naphthyl)-5-phenyl-1,3-thiazol-2-yl]pyridine,
(2E)-3-[5-(4-nitrophenyl)-2-furyl]-1-phenyl-2-propen-1-one,
2-chloro-5-nitro-N-(4- { [2-(pyridin-3-yl)piperidin- 1-yl]sulfonyl}phenyl)benzamide,
N-(4-chloro-2-methylphenyl)-2-[(3,4-dimethoxyphenyl)phenylsulfonyl]amino]acetamide, and
N-[3-(1,3-benzothiazol-2-yl)-6-isopropyl-4,5,6,7-tetrahydrothieno[2,3-c]pyridin-2-yl]-3,5-dimethoxybenzamide,
or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 8,101,580 B2 |
| APPLICATION NO. | : 11/911668 |
| DATED | : January 24, 2012 |
| INVENTOR(S) | : Mayumi Yamano |

It is certified that error appears in the above-identified patent and that said Letters Patent is hereby corrected as shown below:

ON THE TITLE PAGE [56] REFERENCES CITED:

Line 10, Other Publications, under Talley "Pharmcologic" should read --Pharmacologic--.

COLUMN 1:

Line 13, "defecation-trouble" should read --defecation trouble--;
Line 15, "despite of" should read --despite--;
Line 22, "advices" should read --care--;
Line 23, "in female" should read --in females--;
Line 24, "the human" should be deleted;
Line 25, "con-" should be deleted;
Line 26, "cerned" should read --involved--;
Line 30, "are worsen" should read --are worsened--;
Line 41, "too" should be deleted;
Line 45, "there is" should read --is there--;
Line 58, "and they" should read --which--; and
Line 59, "predominant" (second occurrence) should read --predominant IBS--.

COLUMN 2:

Line 1, "predominant" should read --predominant IBS--; and
Line 42, "defication" should read --defecation--.

COLUMN 3:

Line 43, "also" should be deleted; and
Line 57, "486396-92-3) are" should read --486396-92-3) ¶ are--.

Signed and Sealed this
Seventeenth Day of April, 2012

David J. Kappos
*Director of the United States Patent and Trademark Office*

CERTIFICATE OF CORRECTION (continued)
U.S. Pat. No. 8,101,580 B2

COLUMN 5:

Line 1, "defication" should read --defecation--.

COLUMN 7:

Line 36, "TBS" should read --IBS--.

COLUMN 8:

Line 18, "abdominal uncomfortable" should read --uncomfortable abdominal--.

COLUMN 11:

Line 30, "Defication" should read --Defecation--;
    Line 45, "defication," should read --defecation,--;
    Line 47, "defication" should read --defecation--;
    Line 49, "defication" should read --defecation--;
    Line 57, "Defication" should read --Defecation--; and
    Line 65, "per once" should read --once--.

COLUMN 12:

Line 12, "defication" should read --defecation--; and
    Line 28, "of around" should read --through--.

COLUMN 16:

Line 27, "in both" should read --in treating--; and
    Line 28, "of an" should read --an--.

CERTIFICATE OF CORRECTION (continued)
U.S. Pat. No. 8,101,580 B2

COLUMNS 17-18:

Lines 2-19,

"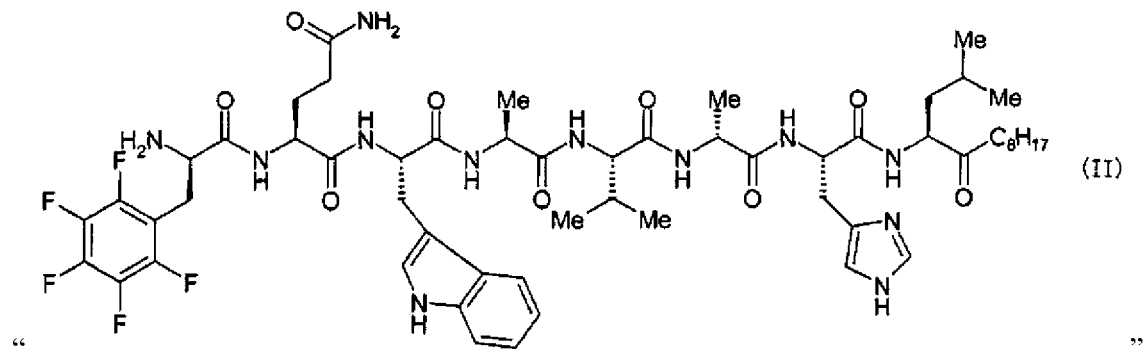 (II)"

should read

--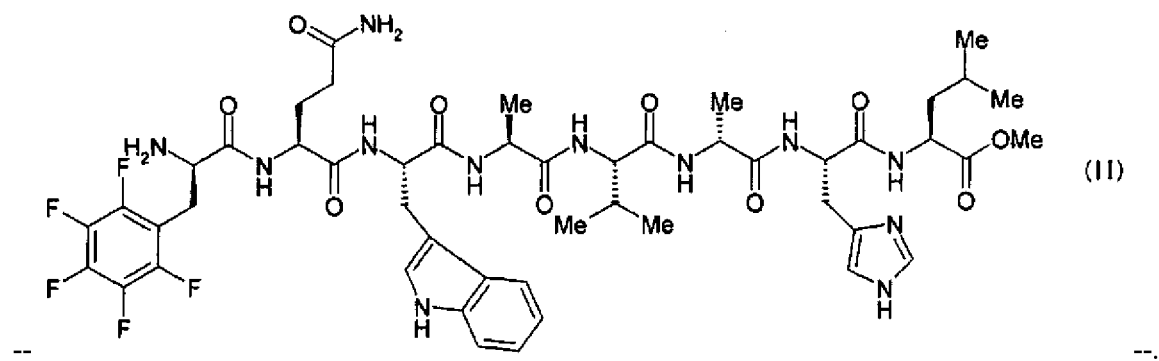 (II)--.